(12) United States Patent
Nakamura

(10) Patent No.: US 8,530,556 B2
(45) Date of Patent: Sep. 10, 2013

(54) ANTIBACTERIAL COSMETIC APPLICATOR

(75) Inventor: Kenji Nakamura, Osaka (JP)

(73) Assignees: Kenji Nakamura, Osaka (JP); Koji Nakamura, Osaka (JP)

( * ) Notice: Subject to any disclaimer, the term of this patent is extended or adjusted under 35 U.S.C. 154(b) by 0 days.

(21) Appl. No.: 13/566,931

(22) Filed: Aug. 3, 2012

(65) Prior Publication Data

US 2012/0295984 A1 Nov. 22, 2012

Related U.S. Application Data

(62) Division of application No. 12/667,014, filed as application No. PCT/JP2009/053911 on Mar. 3, 2009, now abandoned.

(30) Foreign Application Priority Data

Mar. 3, 2008 (JP) .................................. 2008-51759

(51) Int. Cl.
*C08K 5/13* (2006.01)
*C08K 5/20* (2006.01)
*C08K 5/136* (2006.01)

(52) U.S. Cl.
USPC ........... 524/236; 524/241; 524/251; 524/323; 524/339; 524/341; 524/343; 524/350; 524/351; 524/352; 523/122; 514/642; 514/643

(58) Field of Classification Search
USPC ................. 523/122; 524/251, 323; 514/642, 514/643
See application file for complete search history.

(56) References Cited

U.S. PATENT DOCUMENTS

| 5,261,426 A | 11/1993 | Kellett et al. |
| 7,752,702 B2 | 7/2010 | Nakamura et al. |
| 2006/0088711 A1 | 4/2006 | Nakamura et al. |

FOREIGN PATENT DOCUMENTS

| EP | 1 228 717 A2 | 8/2002 |
| EP | 1 591 010 A2 | 11/2005 |
| JP | 46-10518 A | 3/1971 |
| JP | 03-003226 A | 1/1991 |
| JP | 03-289905 A | 12/1991 |
| JP | 04-193103 A | 7/1992 |
| JP | 05-007510 A | 1/1993 |
| JP | 10-005044 A | 1/1998 |
| JP | 10-120821 A | 5/1998 |
| JP | 2000-041730 A | 2/2000 |
| JP | 2002-223857 A | 8/2002 |
| JP | 2005-53973 A | 3/2005 |
| JP | 2005-323953 A | 11/2005 |

OTHER PUBLICATIONS

Supplementary European Search Report mailed by European Patent Office in the corresponding European Patent Application No. 09716246.5 on May 25, 2012.

*Primary Examiner* — Kriellion Sanders
(74) *Attorney, Agent, or Firm* — Knobbe, Martens, Olson & Bear LLP

(57) ABSTRACT

Antibacterial cosmetic brush hairs include synthetic fibers treated with quaternary ammonium salt, phenolic compound, and acid. The antibacterial cosmetic brush hairs inhibit the loss of the antibacterial effect through washing or the like.

11 Claims, No Drawings

ANTIBACTERIAL COSMETIC APPLICATOR

CROSS-REFERENCE TO RELATED APPLICATIONS

This is a divisional application of U.S. patent application Ser. No. 12/667,014, filed Aug. 17, 2010, mow abandoned, which is the U.S. National Phase under 35 U.S.C. §371 of International Application PCT/JP2009/053911, filed Mar. 3, 2009, which claims priority to Japanese Patent Application No. 2008-051759, filed Mar. 3, 2008. The International Application was published under PCT Article 21(2) in a language other than English.

TECHNICAL FIELD

The present invention relates to antibacterial cosmetic brush hairs made of synthetic fibers, as well as an antibacterial cosmetic applicator.

More specifically, the present invention relates to antibacterial cosmetic brush hairs used for cosmetic brushes, mascara brushes, wigs, cosmetic flocked puffs and other cosmetic tools, as well as an antibacterial cosmetic applicator mentioned above which is manufactured by using such antibacterial cosmetic brush hairs.

BACKGROUND ART

There is a strong demand for antibacterial products in recent years in reflection of the growing public interest in cleanliness in various aspects of their life.

Among items of household use, brush hairs (synthetic fibers) used in cosmetic tools such as cosmetic brushes, mascara brushes and other brushes are prone to attachment of sebum, grime, etc., on brush hairs because these brushes are used in a manner coming in direct contact with human hairs, skin, etc., while a liquid or solid cosmetic material is placed on them. When sebum, grime, etc., attach to brush hairs, miscellaneous bacteria and microorganisms grow and foul smell, moulds, etc., generate to create an unsanitary condition. Miscellaneous bacteria and microorganisms also grow on sanitary tools such as toothbrushes and make these tools unsanitary. Accordingly, various proposals have been made to prevent production and growth of miscellaneous bacteria and microorganisms.

Technologies to add antibacterial property to cosmetic tools, sanitary tools, etc., are generally classified into two means. One means of technologies is intended to form a cosmetic tool with brush hairs, etc., from a synthetic resin material, by retaining on the material, before it is processed further, a chemical agent having antibacterial property.

The other means of technologies is intended to use a solution of a chemical agent having antibacterial property to treat the surface of brush hairs or any brush member (such as the base, handle or shaft of the brush) made of a resin material or animal hairs.

Technologies in the former group include, for example, impregnating a chemical agent having antibacterial property into the sheath of hairs each having a two-layer structure constituted by the core and sheath (Patent Literature 1), impregnating one of various chemical agents having antibacterial property into brush hairs (Patent Literatures 2, 3), impregnating a zinc antibacterial agent into brush hairs (Patent Literature 4), and impregnating into brush hairs an inorganic antibacterial agent to which ions of titanium, zirconium or other metal have been added (Patent Literature 5).

Technologies in the latter group include, for example, using an appropriate material selected from alkyl ammonium salt, alkyl benzyl ammonium salt, alkyl pyridinium salt, etc., containing quaternary nitrogen, to give antibacterial treatment to brush hairs made of animal hairs (Patent Literatures 6, 7), and using an appropriate material selected from alkyl ester of parahydroxybenzoate, parachlorophenol, parachlorometacresol, parachlorometaxylenol, isopropyl methylphenol, etc., to give antibacterial treatment (Patent Literature 8).

Patent Literature 1: Japanese Utility Model Laid-open No. Hei 3-3226
Patent Literature 2: Japanese Patent Laid-open No. Hei 3-289905
Patent Literature 3: Japanese Patent Laid-open No. Hei 5-7510
Patent Literature 4: Japanese Patent Laid-open No. Hei 10-5044
Patent Literature 5: Japanese Patent Laid-open No. 2005-53973
Patent Literature 6: Japanese Patent Laid-open No. Hei 4-193103
Patent Literature 7: Japanese Patent Laid-open No. 2002-223857
Patent Literature 8: Japanese Patent Laid-open No. 2000-41730

SUMMARY OF THE INVENTION

Problems to be Solved by the Invention

As explained above, technologies in the former group are intended to form a cosmetic tool, etc., having brush hairs, etc., by mixing an inorganic or organic antibacterial agent into a synthetic resin material to produce a polymer blend. For the aforementioned brush hairs to exhibit antibacterial property, the concentration of antibacterial agent at the surface of brush hairs must be kept at least to a level at which antibacterial effect is exhibited. To this end, the amount of antibacterial agent added to the synthetic resin material must be increased, which necessitates a higher production cost. There are other problems, as well, such as the manufacturing process becoming complicated or the antibacterial agent breaking down at temperatures near the melting temperature of the synthetic resin to produce harmful substances.

On the other hand, technologies in the latter group are associated with a good work efficiency, if animal hairs are used as brush hairs, because antibacterial property can be added simply by soaking the brush hairs in a solution of a chemical agent having antibacterial property.

However, the antibacterial agent adsorbed to the surface of brush hairs quickly runs off when the brush is washed, cleaned, etc., which presents such problems as lower launderability and antibacterial effect not sustained for a long period. If a synthetic resin material is used for brush hairs, on the other hand, it becomes very difficult to add antibacterial property because it cannot be done simply by soaking in a solution of a chemical agent, and launderability becomes also low and antibacterial effect is not sustained for a long period, either.

In light of the situations explained above, the object of the present invention is to provide antibacterial cosmetic brush hairs and antibacterial cosmetic applicators that can be manufactured with ease, prevent loss of antibacterial property after washing, etc., and allow antibacterial property to be sustained for a long period.

Means for Solving the Problems

To solve the aforementioned object, the inventor found, after a series of earnest studies, that the aforementioned object could be solved by using a specified chemical agent to give antibacterial treatment to synthetic fibers, and consequently completed the present invention.

To be specific, the present invention provides antibacterial cosmetic brush hairs characterized in that they are made of synthetic fibers treated with quaternary ammonium salt and phenolic compound.

Antibacterial cosmetic brush hairs having the aforementioned structure prevent the chemical agent from running off after washing and thus demonstrate an excellent effect in terms of antibacterial property lasting for a long period, due to use of the two chemical agents of quaternary ammonium salt and phenolic compound in the impregnation or other process and surface treatment.

Under the present invention, it is desirable that the synthetic fibers be made of one or two or more types of materials selected from polyethylene terephthalate, polybutylene terephthalate, polytrimethylene terephthalate and nylon.

In addition, the synthetic fibers are treated by combining quaternary ammonium salt and phenolic compound to favorably give antibacterial treatment to the synthetic fibers.

Also under the present invention, it is desirable that the quaternary ammonium salt used to give antibacterial treatment be one or two or more types of materials selected from alkyl ammonium salt, alkyl benzyl ammonium salt and alkyl pyridinium salt. Furthermore, antibacterial treatment given under the present invention may be implemented in the form of impregnation process or surface treatment by means of soaking in a solution containing any of the aforementioned antibacterial agents.

In addition, it is desirable for any embodiment conforming to the present invention to present an antibacterial halo in an antibacterial test based on JIS L 1902, conducted after at least five cycles of a washing test based on JIS L 1042.

Moreover, the present invention provides an antibacterial cosmetic applicator by using antibacterial cosmetic brush hairs.

The present invention uses a chemical agent blending quaternary ammonium salt and phenolic compound to give antibacterial treatment to synthetic fibers, in order to facilitate permeation of each antibacterial constituent from the surface to inside of synthetic fibers in the impregnation process, while at the same time increasing the concentration of each chemical agent at the surface of synthetic fibers, thereby more effectively preventing the chemical agent from running off after washing and thereby causing the antibacterial property to last for a long period.

Effects of the Invention

Antibacterial cosmetic brush hairs conforming to the present invention are made by treating synthetic fibers with a chemical agent blending quaternary ammonium salt and phenolic compound, to provide excellent effects such as improved launderability as well as antibacterial property lasting for a long period as a result of gradual exudation of the aforementioned chemical agent impregnated in the synthetic fibers.

In addition, antibacterial cosmetic brush hairs conforming to the present invention improve the manufacturing efficiency because they can be manufactured with an easy operation, while allowing the manufacturing cost to be lowered, as well.

By manufacturing a cosmetic applicator using these antibacterial cosmetic brush hairs, a cosmetic applicator demonstrating excellent antibacterial property can be provided.

BEST MODE FOR CARRYING OUT THE INVENTION

Embodiments of antibacterial cosmetic brush hairs are explained below.

Antibacterial cosmetic brush hairs conforming to the embodiments explained below are produced by treating synthetic fibers with an antibacterial constituent made of quaternary ammonium salt and phenolic compound.

The aforementioned synthetic fibers should preferably be made of one or two or more types of materials selected from polyethylene terephthalate, polybutylene terephthalate, polytrimethylene terephthalate and nylon.

Polyethylene terephthalate, polybutylene terephthalate, polytrimethylene terephthalate and nylon are much more difficult to give antibacterial treatment to, compared to animal hairs, etc., but in the embodiments explained below a two-constituent type chemical agent combining quaternary ammonium salt and phenolic compound is used to give this treatment to achieve not only launderability, but also antibacterial property which lasts for a long period.

The aforementioned quaternary ammonium salt may be any general quaternary ammonium salt, but alkyl ammonium salt, alkyl benzyl ammonium salt and alkyl pyridinium salt are more preferable.

The quaternary ammonium salt may be used alone or two or more types may be combined together.

The aforementioned alkyl ammonium salt, alkyl benzyl ammonium salt and alkyl pyridinium salt have been widely used for many years as surface active agents, and are known to demonstrate excellent antibacterial property and inherently have deodorizing property as well.

For example, alkyl ammonium salt may be alkyl trimethyl ammonium salt or dialkyl dimethyl ammonium salt, alkyl benzyl ammonium salt may be alkyl dimethyl benzyl ammonium salt, and alkyl pyridinium salt may be salt constituted by a pyridine ring bonded with an alkyl group, where the quaternary nitrogen forms a positive ion and halogen atom of chlorine or bromine forms a negative ion, as expressed by the formula (R3N+-R)X—.

Examples of the alkyl ammonium salt include, among others: trimethyl alkyl ammonium salt, or specifically trimethyl decyl ammonium chloride, trimethyl dodecyl ammonium chloride, trimethyl tetradecyl ammonium chloride, trimethyl hexadecyl ammonium chloride, trimethyl octadecyl ammonium chloride, trimethyl decyl ammonium bromide, trimethyl dodecyl ammonium bromide, trimethyl tetradecyl ammonium bromide, trimethyl hexadecyl ammonium bromide, trimethyl octadecyl ammonium bromide, etc.; and dialkyl dimethyl ammonium chloride, or specifically dimethyl dioctyl ammonium chloride, dimethyl didecyl ammonium chloride, dimethyl didodecyl ammonium chloride, dimethyl ditetradecyl ammonium chloride, etc.

Specific examples of the alkyl benzyl ammonium salt include dodecyl dimethyl benzyl ammonium chloride, tetradecyl dimethyl benzyl ammonium chloride, cetyl dimethyl benzyl ammonium chloride, octadecyl dimethyl benzyl ammonium chloride, dodecyl dimethyl benzyl ammonium bromide, tetradecyl dimethyl benzyl ammonium bromide, cetyl dimethyl benzyl ammonium bromide, octadecyl dimethyl benzyl ammonium bromide, palm alkyl dimethyl benzyl ammonium chloride, etc.

Furthermore, specific examples of the alkyl pyridinium salt include lauryl pyridinium chloride, cetyl pyridinium chloride, etc.

Antibacterial cosmetic brush hairs conforming to the present invention should preferably contain the aforementioned quaternary ammonium salt by 0.1 to 5.0 percent by weight. This impregnation amount can be obtained from the rate of increase in the bone dry weight of material after the treatment compared to before the treatment. Antibacterial property is sustained for a long period as long as the processed amount of the quaternary ammonium salt is within the aforementioned range.

The aforementioned phenolic compound may be any compound having a phenolic structure or other structure containing a modified phenolic hydroxyl group, where examples of the phenolic compound include hydroxybenzoic acid, derivative of hydroxybenzoic acid, and compound whose structure contains a chemically modified phenolic hydroxyl group.

Examples of the derivative of hydroxybenzoic acid include, among others, p-hydroxybenzoate methyl, p-hydroxybenzoate ethyl, p-hydroxybenzoate propyl, p-hydroxybenzoate isobutyl, p-hydroxybenzoate butyl, etc. On the other hand, examples of the compound having a phenolic structure or compound whose structure contains a chemically modified phenolic hydroxyl group include phenoxy ethanol, p-amino salicylic acid, thymol, o-chlorothymol, 4-chloro-m-cresol, p-chlorometaxylenol, dichloro-m-xylenol, chlorophenesin, p-chlorophenol, o-phenyl phenol, 4-chloro-m-cresol, 2,2-thiobis (4-chlorophenol), fenticlor, hexachlorophene, cross amide, etc. Take note that these phenolic compounds may be used alone or two or more types may be combined together.

These compounds easily produce a solid solution. For example, when they are used to treat synthetic fibers the synthetic fibers tend to swell and therefore the impregnated amount of fibers increases. This is likely the reason why a lot of quaternary ammonium salt can be impregnated.

Antibacterial cosmetic brush hairs conforming to the present invention should preferably contain the aforementioned phenolic compound by 0.1 to 5.0 percent by weight. This impregnation amount can be obtained from the rate of increase in the bone dry weight of material after the treatment compared to before the treatment. Antibacterial property is sustained for a long period as long as the processed amount of the phenolic compound is within the aforementioned range.

The embodiments explained below are characterized in that a two-constituent agent combining the aforementioned quaternary ammonium salt and phenolic compound is used to give antibacterial treatment.

If impregnation is implemented in a bath, for example, the aforementioned quaternary ammonium salt should be blended preferably by 0.1 to 2.0 o.w.s. percent or more preferably by 0.3 to 0.5 o.w.s. percent. The phenolic compound should be blended preferably by 0.01 to 0.5 o.w.s. percent or more preferably by 0.05 to 0.2 o.w.s. percent.

Here, "o.w.s. percent" indicates the concentration of chemical agent relative to solvent used. If 1 kg of water is used as solvent and 10 g of chemical agent is used, for example, the concentration of chemical agent becomes 1 o.w.s. percent.

If impregnation is implemented by means of steam heating, on the other hand, preferably the aforementioned quaternary ammonium salt should be blended by approx. 5.0 to 20.0 o.w.s. percent and phenolic compound by approx. 0.5 to 10.0 o.w.s. percent.

As long as the blending amount of the aforementioned chemical agent is within the ranges explained above, antibacterial property is sustained for a long period and antibacterial cosmetic brush hairs offering excellent launderability can be obtained.

Combined use of two constitutes, namely quaternary ammonium salt and phenolic compound, results in long-lasting antibacterial property and excellent launderability even when antibacterial treatment is given to synthetic fibers made of polyethylene terephthalate, polybutylene terephthalate, polytrimethylene terephthalate, nylon, etc., that are normally difficult to give antibacterial treatment to.

In general, using a solution system to cause an antibacterial agent constituted by quaternary ammonium salt to act upon synthetic fibers made of polyethylene terephthalate, polybutylene terephthalate, polytrimethylene terephthalate, nylon, etc., results in the quaternary ammonium salt running off after only one washing and the antibacterial property dropping significantly, because the quaternary ammonium salt is only attached to the surface of the synthetic fibers. This is probably because the quaternary ammonium salt is simply attached to the surface of synthetic fibers, instead of permeating through to the inside of synthetic fibers, and thus antibacterial property drops quite easily.

It should be noted, however, that the aforementioned mechanism is only an estimation and this is not the only explanation of the mechanism that may be at work.

In the embodiments explained below, use of a two-constituent type chemical agent combining quaternary ammonium salt and phenolic compound not only allows the agent to attach to the surface of synthetic fibers, but the aforementioned two constituents that are used in combination permeate through to the inside of synthetic fibers, which is probably why excellent launderability and long-lasting antibacterial property can be achieved.

Gradual exudation, to the surface of synthetic fibers, of the chemical agent that has been permeated through to the inside of synthetic fibers is a likely reason why antibacterial property is sustained for a long period.

Also note that, although the aforementioned mechanism is only an estimation, excellent launderability has been demonstrated. However, this is not the only explanation of the mechanism that may be at work.

The aforementioned launderability and long-term antibacterial property are demonstrated by an antibacterial halo obtained by an antibacterial test based on JIS L 1902, conducted after at least five cycles of a washing test based on JIS L 1042. Normally animal hairs can be given a sustainable antibacterial effect when treated with quaternary ammonium salt. If synthetic fibers are treated with quaternary ammonium salt in the same manner, however, the antibacterial halo virtually disappears after only one cycle of washing test. In the embodiments explained below, on the other hand, an antibacterial halo of 3 mm or more is maintained even after five cycles of washing test performed on synthetic fibers that have been given antibacterial treatment, and this is because of combined use of two constituents or namely quaternary ammonium salt and phenolic compound.

Here, the washing test based on JIS L 1042 involves soaking a test sample for 30 minutes in a 0.5 percent-by-weight solution of neutral detergent that has been adjusted to 40° C. ("0.5 percent-by-weight solution" is equivalent to "5 o.w.s. percent") and then washing the sample 100 times by rubbing it with hands, where the foregoing process constitutes one cycle. Accordingly, five washing test cycles mean that the test sample is washed 500 times by rubbing it with hands.

On the other hand, the antibacterial halo test based on JIS L 1902 involves placing and retaining a washed test sample on an agar culture medium containing gram-positive bacteria (*Staphylococcus aureus*).

Antibacterial cosmetic brush hairs in the embodiments explained below can be manufactured by mixing synthetic fibers with water, which is used as solvent, while their respective volumes are adjusted to a specified bath ratio, and then heating the mixture, adding and dissolving quaternary ammonium salt and phenolic compound at specified concentrations, and subsequently adjusting the reaction liquid to acidity and maintaining this acidity for a specified time to give antibacterial treatment to the fibers, and thereafter washing the fibers with water and then drying them.

It is also possible to dissolve quaternary ammonium salt and phenolic compound at high concentrations, soak synthetic resins in this chemical solution at normal temperature and wringing the fibers to a specified ratio, and then steam-heating the fibers using wet, hot steam to give antibacterial treatment to the fibers.

First, a method of manufacturing antibacterial cosmetic brush hairs whereby synthetic fibers are heated in a chemical solution blending quaternary ammonium salt and phenolic compound to give antibacterial treatment to the synthetic fibers, is explained.

In this embodiment, water is used as solvent, just like when cationic dyes are dissolved in water to produce dye solutions. By using water as solvent, safety improves dramatically, while the manufacturing cost also drops significantly, compared to when an organic solvent is used.

When giving antibacterial treatment to synthetic fibers in a bath, the bath ratio relative to water should preferably be 1:5 to 1:25, or more preferably be 1:10 to 1:20. As long as the bath ratio is within the above ranges, the antibacterial agent permeates from the surface to inside of synthetic fibers and adsorbs to the fibers easily.

The "bath ratio" refers to the amount of water (kg) used per 1 kg of brush hairs. For example, a bath ratio of 1:15 means that 15 kg of water is used per 1 kg of brush hairs.

An inorganic acid or organic acid can be used as a chemical agent to adjust the aforementioned reaction liquid to acidity. Examples of inorganic acids include hydrochloric acid, sulfuric acid, etc. Examples of organic acids include acetic acid, formic acid, etc.

It is estimated that as long as the use amount of the aforementioned inorganic acid or organic acid is within the aforementioned ranges, the acid precipitation effect of the antibacterial agent, which is a cationic active agent, causes the aforementioned constituents to adsorb easily to synthetic fibers.

The reaction temperature should preferably be in a range of 90 to 110° C. when antibacterial treatment is given in the solution. The antibacterial treatment in the solution should preferably last for 1 hour or more. As for the condition for reaction, it may be implemented at normal pressure or under pressurization.

In this embodiment, antibacterial treatment ends in a very short period of time, which has the effect of increasing the manufacturing efficiency while lowering the manufacturing cost.

At the end of antibacterial treatment, the synthetic fibers thus impregnated with the chemical agent are washed in water and dried to obtain antibacterial cosmetic brush hairs conforming to the present invention. The manufacturing method in this embodiment uses no organic solvent in any of the processes and is therefore safe and also makes it easy to give post-treatment after the antibacterial treatment.

Next, a method of manufacturing antibacterial cosmetic brush hairs whereby synthetic fibers are soaked in a chemical solution blending quaternary ammonium salt and phenolic compound, the synthetic fibers are wrung to a specified ratio, and then the wrung synthetic fibers are steam-heated to give antibacterial treatment, is explained.

To impregnate the chemical agent using steam heat, synthetic fibers are soaked in a chemical solution of high concentration (containing quaternary ammonium salt by approx. 5.0 to 20.0 o.w.s. percent and phenolic compound by approx. 0.5 to 10.0 o.w.s. percent), after which the synthetic fibers are wrung to a specified ratio and the wrung synthetic fibers are placed in a steam heater to be heated using steam. This way, the use amount of chemical solution decreases to around one-tenth and loss of chemical solution can be reduced.

The aforementioned wringing ratio should preferably be 50 to 150%. When impregnating the chemical agent using steam heat, it is preferable to implement the process under pressurization at 120° C. or below for around 1 hour. As for the wringing ratio, a condition where 100 g of chemical solution is impregnated into 100 g of synthetic fibers in dry, dead weight corresponds to a wringing ratio of 100%.

Antibacterial cosmetic brush hairs in this embodiment are used for antibacterial cosmetic applicators, primarily cosmetic brushes, mascara brushes, wigs, cosmetic flocked puffs, etc. Antibacterial cosmetic brush hairs in this embodiment are also used for antibacterial sanitary tools such as toothbrushes, inter-dental brushes, etc. By using antibacterial cosmetic brush hairs in this embodiment for antibacterial cosmetic applicators and antibacterial sanitary tools like those mentioned above, their antibacterial property is sustained for a long period due to excellent launderability, which makes these tools very sanitary.

With antibacterial cosmetic brush hairs conforming to the present invention, a two-constituent chemical agent combining quaternary ammonium salt and phenolic compound acts upon synthetic fibers where the phenolic compound causes the synthetic fibers to swell, and as a result the antibacterial agent constituted by phenolic compound and quaternary ammonium salt is adsorbed inside the synthetic fibers. Consequently, the bleeding (migration) action of the adsorption material causes the antibacterial agent to gradually release from the inside to outside of fibers, leading to long-lasting antibacterial property as well as excellent launderability.

Also, antibacterial cosmetic brush hairs conforming to the present invention can be manufactured through the simple operation of soaking fibers in a chemical agent solution having antibacterial property, which has the effect of improving the manufacturing efficiency while also lowering the manufacturing cost.

Another benefit of the present invention is that antibacterial treatment can be given with ease to synthetic fibers made of polyethylene terephthalate, polybutylene terephthalate, polytrimethylene terephthalate, nylon, etc., that have traditionally been considered difficult to give antibacterial treatment to.

Note that antibacterial cosmetic brush hairs conforming to the present invention will present no problems at all when combined with animal hairs to be given antibacterial treatment, and the combined brush hairs thus obtained can be used to manufacture antibacterial cosmetic applicators.

EXAMPLES

Antibacterial cosmetic brush hairs conforming to the present invention are explained below based on examples. It should be noted, however, that the present invention is not at all limited to these examples.

(Washing Test Method Based on JIS L 1042 (1972))

Soak a test sample in a 40° C. neutral detergent solution (0.5 percent-by-weight solution) for 30 minutes, and then wash the test sample by rubbing it with hands. The foregoing constitutes one washing test cycle and this cycle is repeated 100 times.

(Halo Width Measurement Test Based on JIS L 1902 (1980))

A filament made of synthetic fibers to be used as brush hairs was looped once around a glass slide of 38×26 mm in size, at the center of the slide, to a width of 28 mm to create a test sample.

On the other hand, 1 ml of gram-positive bacteria (*Staphylococcus aureus*) and 15 ml of an agar culture medium that has been kept at approx. 45° C. are mixed on a Petri dish and then the mixture was solidified at room temperature. Next, the Petri dish was inverted to vaporize excess water.

The aforementioned test sample was smeared onto the surface of this culture medium and the medium was inverted and cultured at 37° C. for 24 hours or 48 hours. After the culture test, the width of the halo produced around the test sample was measured to obtain the halo width (W) using the formula below:

$$W=(T-D)/2$$

(Here, T represents the sum of the length of the test piece and halo width, while D represents the length of the test piece.)

Example 1

Using polybutylene terephthalate (0.07 mm in diameter, tapered bristles) as synthetic fibers and water as solvent, the polybutylene terephthalate was soaked in the water at a bath ratio adjusted to 1:15 and then the mixture was heated, after which 0.5 o.w.s. percent of dodecyl trimethyl ammonium chloride (trade name: Cation BB, manufactured by NOF Corporation) and 0.1 o.w.s. percent of phenolic compound (trade name: Phenonip, manufactured by Clariant Japan K.K.) were dissolved, and then 0.05 o.w.s. percent of acetic anhydride was added to achieve acetic acidity, to give antibacterial treatment to polybutylene terephthalate at 92° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush.

When the obtained cosmetic brush was measured for halo width using gram-positive bacteria (*Staphylococcus aureus*) in conformance with JIS L 1902, the measured halo width was 12 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 4 mm.

Note that Phenonip used in this example is an antibacterial agent produced by mixing phenoxy ethanol and paraben, where the specific composition is 70 to 75 percent by weight of phenoxy ethanol, 14.5 to 16.5 percent by weight of p-hydroxybenzoate methyl (methyl paraben), 3.5 to 4.3 percent by weight of p-hydroxybenzoate ethyl (ethyl paraben), 1.7 to 2.3 percent by weight of p-hydroxybenzoate propyl (propyl paraben), 3.7 to 4.3 percent by weight of p-hydroxybenzoate butyl (butyl paraben), and 1.7 to 2.3 percent by weight of p-hydroxybenzoate isobutyl (isobutyl paraben).

Example 2

Using 3-mm piled velvet made of polytrimethylene terephthalate (2 dtex, 36 filament) fibers as synthetic fibers and water as solvent, the velvet was soaked in the water at a bath ratio adjusted to 1:25 and then the mixture was heated, after which 1.0 o.w.s. percent of lauryl dimethyl benzyl ammonium chloride (trade name: Sanisol C, manufactured by Kao Corporation) and 0.3 o.w.s. percent of p-hydroxybenzoate methyl (methylparaben, manufactured by Iwasaki Cosfa Co., Ltd.) were dissolved, and then 0.05 o.w.s. percent of acetic anhydride was added to achieve acetic acidity, to give antibacterial treatment to velvet at 93° C. for 60 minutes.

At the end of antibacterial treatment, the velvet was washed in water and dried to obtain antibacterial velvet. The antibacterial velvet was used to create a cosmetic puff. When this cosmetic puff was measured for halo width using gram-positive bacteria (*Staphylococcus aureus*) in conformance with JIS L 1902, the measured halo width was 8 mm or more.

Next, the velvet was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 4 mm.

Example 3

Using polybutylene terephthalate (0.07 mm in diameter, tapered bristle) as synthetic fibers and water as solvent, the polybutylene terephthalate was soaked in the water at a bath ratio adjusted to 1:15 and then the mixture was heated, after which 0.7 o.w.s. percent of lauryl dimethyl benzyl ammonium chloride (trade name: Sanisol C, manufactured by Kao Corporation) and 0.1 o.w.s. percent of p-aminosalicylic acid (guaranteed reagent) were dissolved, and then 0.05 o.w.s. percent of acetic anhydride was added to achieve acetic acidity, to give antibacterial treatment to polybutylene terephthalate at 110° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 4 mm.

Example 4

Using polytrimethylene terephthalate (0.07 mm in diameter) fibers as synthetic fibers and water as solvent, the polytrimethylene terephthalate fibers were soaked in the water at a bath ratio adjusted to 1:15 and then the mixture was heated, after which 0.5 o.w.s. percent of dodecyl trimethyl ammonium chloride (trade name: Cation BB, manufactured by NOF Corporation) and 0.1 o.w.s. percent of phenolic compound (trade name: Phenonip, manufactured by Clariant Japan K.K.) were dissolved, and then 0.05 o.w.s. percent of acetic anhydride was added to achieve acetic acidity, to give antibacterial treatment to polytrimethylene terephthalate at 92° C. for 60 minutes.

At the end of antibacterial treatment, the polytrimethylene terephthalate fibers were washed in water and dried to obtain antibacterial polytrimethylene terephthalate fibers. The antibacterial polytrimethylene terephthalate fibers were used to create a cosmetic brush.

When the obtained cosmetic brush was measured for halo width using gram-positive bacteria (*Staphylococcus aureus*) in conformance with JIS L 1902, the measured halo width was 10 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 5 mm.

Example 5

Using polytrimethylene terephthalate (0.07 mm in diameter) fibers as synthetic fibers and water as solvent, the polytrimethylene terephthalate fibers were soaked in the water at a bath ratio adjusted to 1:25 and then the mixture was heated, after which 1.0 o.w.s. percent of lauryl dimethyl benzyl ammonium chloride (trade name: Sanisol C, manufactured by Kao Corporation) and 0.1 o.w.s. percent of phenolic compound (trade name: Phenonip, manufactured by Clariant Japan K.K.) were dissolved, and then 0.05 o.w.s. percent of acetic anhydride was added to achieve acetic acidity, to give antibacterial treatment to polytrimethylene terephthalate at 93° C. for 60 minutes.

At the end of antibacterial treatment, the polytrimethylene terephthalate fibers were washed in water and dried to obtain antibacterial polytrimethylene terephthalate fibers. The antibacterial polytrimethylene terephthalate fibers were used to create a cosmetic brush.

When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 4 mm.

Example 6

Using 3-mm piled velvet made of polybutylene terephthalate (2 dtex, 36 filament) fibers as synthetic fibers and water as solvent, 15 o.w.s. percent of dodecyl dimethyl ammonium chloride (trade name: Cation BB, manufactured by NOF Corporation) and 2 o.w.s. percent of phenolic compound (trade name: Phenonip, manufactured by Clariant Japan K.K.) were dissolved, and then 0.5 o.w.s. percent of acetic anhydride was added to achieve acetic acidity. The polybutylene terephthalate velvet was soaked in the obtained solution and then wrung using a rubber-roll mangle to a wringing ratio of 100%, after which the velvet was given antibacterial treatment through steam-heating at 110° C. for 60 minutes.

At the end of antibacterial treatment, the polybutylene terephthalate velvet was washed in water and dried to obtain antibacterial velvet. The antibacterial velvet was used to create a cosmetic flocked puff. When this cosmetic puff was measured for halo width using gram-positive bacteria (*Staphylococcus aureus*) in conformance with JIS L 1902, the measured halo width was 8 mm or more.

Next, the cosmetic puff was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 3 mm or more.

Example 7

Using tapered bristles of polybutylene terephthalate fibers (0.07 mm in diameter) as synthetic fibers, 15 o.w.s. percent of dodecyl dimethyl ammonium chloride (trade name: Cation BB, manufactured by NOF Corporation) and 2 o.w.s. percent of phenolic compound (trade name: Phenonip, manufactured by Clariant Japan K.K.) were dissolved, and then 0.5 o.w.s. percent of acetic anhydride was added to achieve acetic acidity. The bristles were soaked in the obtained solution and then set in a centrifugal dehydrator. The centrifugal dehydrator was operated for 20 seconds to achieve a wringing ratio of 100%, after which the bristles were removed and set in a steam heater to be given antibacterial treatment through steam-heating at 110° C. for 60 minutes. At the end of antibacterial treatment, these bristles were washed in water and dried to obtain antibacterial bristles. The obtained bristles were used to create a cosmetic powder brush. When this cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 3 mm or more.

Example 8

Using polytrimethylene terephthalate (0.07 mm in diameter) fibers as synthetic fibers, 15 o.w.s. percent of dodecyl dimethyl ammonium chloride (trade name: Cation BB, manufactured by NOF Corporation) and 2 o.w.s. percent of p-chlorometaxylenol (manufactured by Clariant) were dissolved, and then 0.5 o.w.s. percent of acetic anhydride was added to achieve acetic acidity. The fibers were soaked in the obtained solution and then set in a centrifugal dehydrator. The centrifugal dehydrator was operated for 20 seconds to achieve a wringing ratio of 100%, after which the fibers were removed and set in a steam heater to be given antibacterial treatment through steam-heating at 110° C. for 60 minutes. At the end of antibacterial treatment, these fibers were washed in water and dried to obtain antibacterial fibers. The obtained fibers were used to create a cosmetic brush. When this cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. The measured halo width was 3 mm or more.

Comparative Example 1

Using polybutylene terephthalate (0.10 mm in diameter, tapered bristles) as synthetic fibers and water as solvent, the polybutylene terephthalate was soaked in the water at a bath ratio adjusted to 1:15 and then the mixture was heated, after which 0.7 o.w.s. percent of lauryl dimethyl benzyl ammonium chloride (trade name: Sanisol C, manufactured by Kao Corporation) was dissolved, and then 0.05 o.w.s. percent of acetic anhydride was added to achieve acetic acidity, to give antibacterial treatment to polybutylene terephthalate at 110° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result shows that the antibacterial property dropped significantly compared before washing, meaning that the antibacterial agent had attached simply in a manner having no launderability at all.

Comparative Example 2

Using polybutylene terephthalate (0.10 mm in diameter, tapered bristles) as synthetic fibers and water as solvent, the polybutylene terephthalate was soaked in the water at a bath ratio adjusted to 1:15 and then the mixture was heated, after which 0.7 o.w.s. percent of dodecyl trimethyl benzyl ammonium chloride (trade name: Cation BB, manufactured by NOF Corporation) was dissolved, and then 0.05 o.w.s. percent of acetic anhydride was added to achieve acetic acidity, to give antibacterial treatment to polybutylene terephthalate at 110° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result confirms that the antibacterial property dropped significantly compared before washing.

Comparative Example 3

Using polybutylene terephthalate (0.10 mm in diameter, tapered bristles) as synthetic fibers and water as solvent, the polybutylene terephthalate was soaked in the water at a bath ratio adjusted to 1:15 and then the mixture was heated, after which 0.7 o.w.s. percent of hexadecyl trimethyl ammonium chloride (trade name: Quartamin 60W, manufactured by Kao Corporation) was dissolved, and then 0.05 o.w.s. percent of acetic anhydride was added to achieve acetic acidity, to give antibacterial treatment to polybutylene terephthalate at 110° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result confirms that the antibacterial property dropped significantly compared before washing.

Comparative Example 4

Using polytrimethylene terephthalate (0.07 mm in diameter) fibers as synthetic fibers and water as solvent, the polytrimethylene terephthalate was soaked in the water at a bath ratio adjusted to 1:15 and then the mixture was heated, after which 0.7 o.w.s. percent of lauryl dimethyl benzyl ammonium chloride (trade name: Sanisol C, manufactured by Kao Corporation) was dissolved, and then 0.05 o.w.s. percent of acetic anhydride was added to achieve acetic acidity, to give antibacterial treatment to polytrimethylene terephthalate at 110° C. for 60 minutes.

At the end of antibacterial treatment, the polytrimethylene terephthalate was washed in water and dried to obtain antibacterial polytrimethylene terephthalate. The antibacterial polytrimethylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result shows that the antibacterial property dropped significantly compared before washing, meaning that the antibacterial agent had attached simply in a manner having no launderability at all.

Comparative Example 5

Using polytrimethylene terephthalate (0.07 mm in diameter) fibers as synthetic fibers and water as solvent, the polytrimethylene terephthalate was soaked in the water at a bath ratio adjusted to 1:15 and then the mixture was heated, after which 0.7 o.w.s. percent of dodecyl trimethyl benzyl ammonium chloride (trade name: Cation BB, manufactured by NOF Corporation) was dissolved, and then 0.05 o.w.s. percent of acetic anhydride was added to achieve acetic acidity, to give antibacterial treatment to polytrimethylene terephthalate at 110° C. for 60 minutes.

At the end of antibacterial treatment, the polytrimethylene terephthalate was washed in water and dried to obtain antibacterial polytrimethylene terephthalate. The antibacterial polytrimethylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result confirms that the antibacterial property dropped significantly compared before washing.

Comparative Example 6

Using polybutylene terephthalate (0.10 mm in diameter, tapered bristles) as synthetic fibers and water as solvent, the polybutylene terephthalate was soaked in the water at a bath ratio adjusted to 1:15 and then the mixture was heated, after which 2 o.w.s. percent of phenolic compound (trade name: Phenonip, manufactured by Clariant Japan K.K.) was dissolved, to give antibacterial treatment to polybutylene terephthalate at 110° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush. When the obtained cosmetic brush was measured for halo width using gram-positive bacteria (*Staphylococcus aureus*) in conformance with JIS L 1902, the measured halo width was 7.0 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result shows that the antibacterial property dropped significantly compared before washing, meaning that the antibacterial agent had attached simply in a manner having no launderability at all.

Comparative Example 7

Using 3-mm piled velvet made of polytrimethylene terephthalate (2 dtex, 36 filament) fibers as synthetic fibers and water as solvent, the polytrimethylene terephthalate was soaked in the water at a bath ratio adjusted to 1:15 and then the mixture was heated, after which 2 o.w.s. percent of phenolic compound (trade name: Phenonip, manufactured by Clariant Japan K.K.) were dissolved, to give antibacterial treatment to polytrimethylene terephthalate at 110° C. for 60 minutes.

At the end of antibacterial treatment, the polytrimethylene terephthalate was washed in water and dried to obtain antibacterial polytrimethylene terephthalate. The antibacterial polytrimethylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result shows that the antibacterial property dropped significantly compared before washing, meaning that the antibacterial agent had attached simply in a manner having no launderability at all.

Comparative Example 8

Using polybutylene terephthalate (0.10 mm in diameter, tapered bristles) as synthetic fibers and water as solvent, the polybutylene terephthalate was soaked in the water at a bath ratio adjusted to 1:15 and then the mixture was heated, after which 2 o.w.s. percent of phenolic compound, or specifically p-chlorometaxylenol (manufactured by Clariant) was dissolved, to give antibacterial treatment to polybutylene terephthalate at 110° C. for 60 minutes.

At the end of antibacterial treatment, the polybutylene terephthalate was washed in water and dried to obtain antibacterial polybutylene terephthalate. The antibacterial polybutylene terephthalate was used to create a cosmetic brush. When the obtained cosmetic brush was measured for halo width using gram-positive bacteria (*Staphylococcus aureus*) in conformance with JIS L 1902, the measured halo width was 7.0 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result shows that the antibacterial property dropped significantly compared before washing, meaning that the antibacterial agent had attached simply in a manner having no launderability at all.

Comparative Example 9

Using 3-mm piled velvet made of polytrimethylene terephthalate (2 dtex, 36 filament) fibers as synthetic fibers and water as solvent, the polytrimethylene terephthalate was soaked in the water at a bath ratio adjusted to 1:15 and then the mixture was heated, after which 2 o.w.s. percent of p-hydroxybenzoate methyl (methylparaben, manufactured by Wako Pure Chemical Industries, Ltd.) was dissolved, to give antibacterial treatment to polytrimethylene terephthalate at 110° C. for 60 minutes.

At the end of antibacterial treatment, the polytrimethylene terephthalate was washed in water and dried to obtain antibacterial polytrimethylene terephthalate. The antibacterial polytrimethylene terephthalate was used to create a cosmetic brush. When the obtained cosmetic brush was measured for halo width using gram-positive bacteria (*Staphylococcus aureus*) in conformance with JIS L 1902, the measured halo width was 8 mm or more.

Next, the cosmetic brush was washed 100 times by rubbing it with hands in accordance with the aforementioned washing test and this was repeated five times (for a total of 500 washing cycles), after which the halo width was measured using gram-positive bacteria (*Staphylococcus aureus*) in conformance with JIS L 1902. There was no longer any antibacterial halo.

The above result shows that the antibacterial property dropped significantly compared before washing, meaning that the antibacterial agent had attached simply in a manner having no launderability at all.

(Summary of Examples and Comparative Examples)

When the treatments of synthetic fiber brush hairs using an agent combining quaternary ammonium salt and phenolic compound (Examples 1 to 8) were compared with the treatments using quaternary ammonium salt alone (Comparative Examples 1 to 5) or phenolic compound alone (Comparative Examples 6 to 9), the halo effects achieved by the treatments with single-constituent agents were little different from the halo effects achieved by the treatments with agents combining the above constituents based on measurements taken immediately after the treatment. However, the antibacterial effects became significantly different over time, indicating a clear advantage of combining the above constituents.

What is claimed is:

1. Antibacterial cosmetic brush hairs produced by surface-treating synthetic fibers with an antibacterial agent consisting of quaternary ammonium salt and phenolic compound, and acid, said antibacterial cosmetic brush hairs having long-lasting antibacterial activity such that the antibacterial cosmetic brush hairs can maintain antibacterial activity after being washed five times, each washing consisting of rubbing with hands 100 times, said phenolic compound being one or more compounds selected from the group consisting of hydroxybenzoic acid, p-hydroxybenzoate methyl, p-hydroxybenzoate ethyl, p-hydroxybenzoate propyl, p-hydroxybenzoate isobutyl, p-hydroxybenzoate butyl, phenoxy ethanol, p-aminosalicylic acid, thymol, o-chlorothymol, 4-chloro-m-cresol, p-chlorometaxylenol, dichloro-m-xylenol, chlorophenesin, p-chlorophenol, o-phenyl phenol, 4-chloro-m-cresol, 2,2-thiobis (4-chlorophenol), fenticlor, hexachlorophene, and cross amide.

2. Antibacterial cosmetic brush hairs according to claim 1, wherein the synthetic fibers are made of one or two or more types of materials selected from polyethylene terephthalate, polybutylene terephthalate, polytrimethylene terephthalate and nylon.

3. Antibacterial cosmetic brush hairs according to claim 1, wherein the quaternary ammonium salt is alkyl ammonium salt and/or alkyl benzyl ammonium salt.

4. An antibacterial cosmetic applicator comprising antibacterial cosmetic brush hairs according to claim 1.

5. Antibacterial cosmetic brush hairs according to claim 2, wherein the quaternary ammonium salt is alkyl ammonium salt and/or alkyl benzyl ammonium salt.

6. An antibacterial cosmetic applicator comprising antibacterial cosmetic brush hairs according to claim 2.

7. An antibacterial cosmetic applicator comprising antibacterial cosmetic brush hairs according to claim 3.

8. Antibacterial cosmetic brush hairs according to claim 1, wherein the acid is an inorganic acid or an organic acid.

9. Antibacterial cosmetic brush hairs according to claim 8, wherein the acid is an organic acid which is acetic acid or formic acid.

10. Antibacterial cosmetic brush hairs according to claim 1, wherein the quaternary ammonium salt is contained in an amount of 0.1 to 5.0 percent by weight relative to the weight of the antibacterial cosmetic brush hairs.

11. Antibacterial cosmetic brush hairs according to claim 1, wherein the phenolic compound is contained in an amount of 0.1 to 5.0 percent by weight relative to the weight of the antibacterial cosmetic brush hairs.

* * * * *